United States Patent [19]

Hashizume et al.

[11] Patent Number: 4,562,285

[45] Date of Patent: * Dec. 31, 1985

[54] PROCESS FOR PRODUCING TEREPHTHALIC ACID

[75] Inventors: Hiroshi Hashizume; Yoshiaki Izumisawa, both of Kitakyusya, Japan

[73] Assignee: Mitsubishi Chemical Industries Limited, Tokyo, Japan

[*] Notice: The portion of the term of this patent subsequent to Dec. 24, 2002 has been disclaimed.

[21] Appl. No.: 693,232

[22] Filed: Jan. 22, 1985

Related U.S. Application Data

[63] Continuation of Ser. No. 306,764, Sep. 29, 1981, abandoned, which is a continuation of Ser. No. 860,480, Dec. 14, 1977, abandoned.

[30] Foreign Application Priority Data

Dec. 30, 1976 [JP] Japan .................................. 51-158986
Dec. 30, 1976 [JP] Japan .................................. 51-158988

[51] Int. Cl.$^4$ ............................................... C07C 51/16
[52] U.S. Cl. ................................................... 562/414
[58] Field of Search ......................................... 562/414

[56] References Cited

U.S. PATENT DOCUMENTS 3,996,271 12/1976 Yokoto et al. ...................... 562/414
4,051,178 9/1977 Kimura et al. ..................... 562/414

Primary Examiner—Alan Siegel
Attorney, Agent, or Firm—Oblon, Fisher, Spivak, McClelland & Maier

[57] ABSTRACT

There is disclosed a process for producing terephthalic acid in which the mother liquor of the terephthalic acid slurry resulting from the oxidation of para-xylene, from which terephthalic acid has been separated is subjected to distillation to recover at least a portion of methyl acetate present therein, the recovered methyl acetate being circulated into the reactor.

9 Claims, 1 Drawing Figure

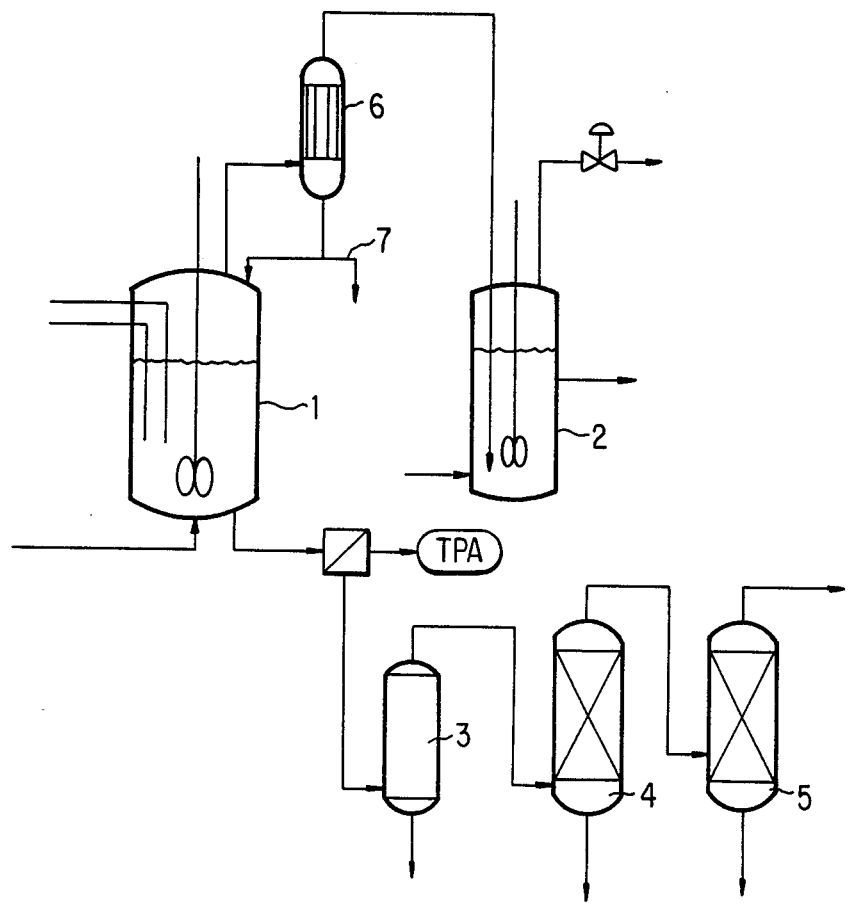

PROCESS FOR PRODUCING TEREPHTHALIC ACID

This application is a continuation of application Ser. No. 306,764, filed Sept. 29, 1981, now abandoned, which is a continuation of abandoned application Ser. No. 860,480, filed Dec. 14, 1977.

BACKGROUND OF THE INVENTION

1. Field of the Invention

This invention relates to a process for producing terephthalic acid by oxidizing para-xylene with molecular oxygen.

2. Description of the Prior Art

Oxidation of para-xylene with molecular oxygen in acetic acid as solvent in the presence of a catalyst system containing bromine and one or more heavy metals such as cobalt, manganese and the like for the preparation of terephthalic acid is well known as the S.D. method. Although this method is satisfactory for the commercial production of terephthalic acid in various respects, there is a problem in that loss of acetic acid as the solvent takes place during the reaction, resulting in enhanced solvent unit, which is a significant disadvantage of the method.

For this acetic acid loss, the following two principal causes are considered: the combustion of acetic acid and the formation of a by-product methyl acetate. Among these, the combustion of acetic acid has previously been investigated in various ways. It has been proposed, for example, to suppress the combustion using specific reaction conditions or a specific catalyst and a certain degree of good results have been obtained thereby. However, the other principal cause for the solvent loss, that is, the formation of the by-product methyl acetate has received little investigation.

SUMMARY OF THE INVENTION

Accordingly, it is an object of this invention to provide a process for suppressing the formation of the by-product methyl acetate.

Briefly, this and other objects of this invention, as will hereinafter be made clear from the ensuing discussion, have been attained by subjecting to distillation the mother liquor of the terephthalic acid slurry resulting from the oxidation of para-xylene so as to recover the methyl acetate present therein after the mother liquor has been separated from terephthalic acid, and then circulating the methyl acetate thus recovered into the oxidation reaction.

BRIEF DESCRIPTION OF THE DRAWING

FIG. 1 shows an experimental equipment as used in the example of this invention, wherein (1) represents a reactor; (2), an absorption vessel; (3), an evaporator; (4), a distillation column for use in acetic acid separation; (5), a distillation column for use in methyl acetate separation; (6), a reflux condenser; and (7), a condensate outlet.

DETAILED DESCRIPTION OF THE PREFERRED EMBODIMENTS

This invention is directed to a process for producing terephthalic acid by oxidizing para-xylene with molecular oxygen in acetic acid as solvent in the presence of a catalyst system containing cobalt, manganese and bromine, characterized by (1) separating solid terephthalic acid from the terephthalic acid slurry resulting from the reaction to form the mother liquor, (2) subjecting the mother liquor to distillation to recover at least a portion of the methyl acetate present therein and then (3) circulating the thus recovered methyl acetate into the reactor.

This invention will be hereinafter described more fully. The production of terephthalic acid contemplated herein includes any process in which para-xylene is oxidized with molecular oxygen in acetic acid solvent in the presence of a catalyst system containing cobalt, manganese and bromine for the production of terephthalic acid.

The reaction conditions suitable for this invention include, usually, a temperature between 150° C. and 250° C., preferably between 180° C. and 220° C. and a pressure in the range of 1 to 50 Kg/cm$^2$, preferably in the range of 10 to 30 Kg/cm$^2$. The residence time in the reaction system is, for example, on the order of 30 to 200 minutes.

Examples of the catalyst components usable in this invention include cobalt compounds such as cobalt acetate, cobalt naphthenate and the like; manganese compounds such as manganese acetate, manganese naphthenate and the like; and bromine compounds such as hydrogen bromide, sodium bromide, cobalt bromide, manganese bromide and the like. If cobalt bromide and/or manganese bromide is used, each of them can function as sources of two catalytic elements.

With respect to the amounts of these catalyst components used, usually the cobalt compounds should preferably be present at the level of 100–500 ppm (as Co metal), the manganese compound at the level of 50–1,000 ppm (as Mn metal) and the bromine compound at the level of 500–3,000 ppm (as Br), each amount being based on the amount of acetic acid solvent.

Usually air is useful for the molecular oxygen used in accordance with this invention and it is provided in a proportion of 3 to 100 moles per mole of para-xylene. The acetic acid solvent is usually used in an amount of 0.5 to 20 parts, preferably 1 to 10 parts, per part of para-xylene (on the weight basis).

It is an essential feature of this invention to recover methyl acetate from the mother liquor of the oxidation reaction mixture by distillation and circulate it into the reactor. The mother liquor of the oxidation reaction mixture always contains the by-product methyl acetate formed during the reaction. In the prior art process, such mother liquor obtained by separating terephthalic acid was subjected to distillation to remove any water and then reused as the solvent. In this case, the methyl acetate present in the mother liquor is also removed and discarded together with water. According to this invention, such water-methyl acetate mixture is redistilled to recover at least a portion of, preferably substantially all of the methyl acetate, which is then circulated into the reactor, whereby the formation of by-product methyl acetate is suppressed. Thus, the increased concentration of methyl acetate in the mother liquor of the oxidation reaction mixture makes it possible to hinder the side reaction that forms methyl acetate from acetic acid.

The distillation procedure according to this invention may be performed by removing terephthalic acid from the reaction mixture to form the mother liquor and then evaporating the mother liquor at atmospheric pressure and, for example, 130° C. so as to vaporize liquid materials such as acetic acid, water, methyl acetate and the like. The vapors are then distilled in a distillation column for use in acetic acid separation at, for example, 100° C. in the top and 120° C. in the bottom so as to recover acetic acid from the bottom and a water-methyl acetate mixture from the top. The mixture is further distilled at atmospheric pressure in a distillation column for use in methyl acetate separation at, for example, 57° C. in the top and 100° C. in the bottom so as to recover methyl acetate from the top. Usually all or substantially all the methyl acetate thus recovered is circulated continuously into the reactor.

In the practice of this invention, since the gas directly evolved from the oxidation reactor also contains methyl acetate, substantially all of such methyl acetate may be recovered and circulated into the reactor to further advantage. The recovery of methyl acetate from the reactor off-gas may be effected by such a procedure as condensation of the gas, although it is favorable to contact the condenser off-gas with acetic acid in order to cause the methyl acetate in the off-gas to be absorbed in the acetic acid for its recovery.

In an ordinary process for producing terephthalic acid on an industrial scale, the water content in the reaction system is in the range of about 17 to 20 percent by weight. However, this invention is applicable to a process wherein the water content is kept at, for example, 5 to 14 percent by weight in order to enhance catalytic activity. In such a process, the control of the water content can be effected by taking out of the reaction system a portion of the condensate obtained by condensing the gas evolved from the reactor. In a preferred embodiment of this invention, the methyl acetate contained in the reaction mother liquor as well as in the reflux condensate is recovered, for example, by a process wherein a mixture of the reaction mother liquor and the reflux condensate is distilled.

As mentioned above, in accordance with the invention, the recovery of methyl acetate in the reaction mother liquor and its circulation into the reactor result in an increase in concentration of methyl acetate in the reactor, which in turn brings about a significant decrease in acetic acid loss due to the formation of by-product methyl acetate. Thus the process according to this invention makes possible the lower acetic acid loss and is quite economical and commercially advantageous on this account.

Having generally described this invention, a more complete understanding can be obtained by comparative examples and examples which are provided herein for purposes of illustration only and are not intended to be limiting in any manner.

EXAMPLE 1

Using an experimental equipment as shown in FIG. 1 (a valve in a condensate outlet pipe (7) is closed), an oxidation reaction was carried out as follows:

Titanium pressure-resisting reactor (1) of 10 l capacity equipped with a reflux condenser device having the condensate outlet (7), a stirring means, a heating device, a starting material inlet, a solvent inlet, an air inlet, a reaction slurry outlet and an off-gas outlet was charged with a solvent-catalyst mixture having the following composition:

| | |
|---|---|
| Acetic acid | 2,990 gr. |
| Cobalt acetate | 4.44 gr. |
| (tetrahydrate) | (330 ppm as Co based on the solvent) |
| Manganese acetate | 4.68 gr. |
| (tetrahydrate) | (330 ppm as Mn based on the solvent) |
| Hydrobromic acid | 6.70 gr. |
| (aqueous 47% solution) | (1,000 ppm as Br based on the solvent) |
| Water | 124 gr. |
| | (5 wt. % water content based on the solvent) |

On the other hand, stainless steel pressure-resisting absorption vessel (2) of 10 l capacity provided with an off-gas sparging inlet, an off-gas outlet, an acetic acid inlet and an acetic acid outlet was charged with 5 l of glacial acetic acid.

First reaction

In order to prepare a terephthalic acid slurry, an oxidation reaction was carried out in reactor (1) at a temperature of 210° C. and a pressure of 25 kg/cm² for 2 hours under stirring at 500 r.p.m. with para-xylene being supplied at a rate of 500 gr./hr. and air being introduced at such a rate that the oxygen content of the oxidation off-gas was maintained at 4% by volume, Subsequently, under the same conditions of temperature, pressure and stirring and with the feed of para-xylene and air in the same way, the reaction was further continued for 24 hours. During this period, a solvent-catalyst mixture of the same composition as above was supplied at a rate of 1,500 gr./hr., while the reaction slurry was intermittently withdrawn from reactor (1) at intervals of 30 minutes to such a level that the volume of the reaction slurrry remaining in the reactor was 4.5 l. The reaction slurry thus withdrawn was filtered to separate terephthalic acid particles and the filtrate or reaction mother liquor was stored in a reservoir. The oxidation off-gas evolved during the reaction was passed through absorption vessel (2) which was operated at a temperature of 30° C. and a pressure of 25 kg/cm² under stirring at 150 r.p.m. From two hours after the start of the reaction, glacial acetic acid was passed to the vessel at a rate of 500 gr./hr., while the acetic acid in the vessel were intermittently withdrawn at intervals of 30 minutes to such a level that the volume of the acetic acid was 5 l. The thus obtained acetic acid in which methyl acetate was absorbed was also stored in another reservoir.

Second reaction

The reaction mother liquor resulting from the first reaction was passed to evaporator (3), in which the liquid materials were completely stripped off at a temperature of 130° C. The overhead vapor was then passed to distillation column (4) for use in the separation of acetic acid, in which it was distilled at an overhead temperature of 100° C. to recover acetic acid from the bottom. The water-methyl acetate mixture as the overhead vapor was then passed to distillation column (5) for use in the separation of methyl acetate, in which it was distilled at an overhead temperature of 57° C. to recover methyl acetate from the overhead.

The thus recovered methyl acetate was admixed with the acetic acid resulting from the first reaction which contained methyl acetate absorbed therein, and in addition the catalyst components and fresh acetic acid were added sufficiently to prepare a solvent-catalyst mixture which had the same composition as above and which additionally contained 13.1 gr. of methyl acetate in each 1,500 gr. amount of the solvent. The reaction was then recommenced with the thus prepared solvent-catalyst mixture under the same conditions as in the first reaction and continued for 10 hours. During this period, the amount of methyl acetate formed was determined and the results are given in Table 1.

Comparative Example 1

During the first reaction of Example 1, the amount of methyl acetate formed was determined. The results are also reported in Table 1.

TABLE 1

|  | MeOAc in reaction mother liquid (gr./hr.) | MeOAc absorbed in acetic acid (gr./hr.) | MeOAc in [1] absorption vessel off-gas (gr./hr.) | MeOAc supplied (gr./hr.) | MeOAc[2] formed (gr./hr.) |
| --- | --- | --- | --- | --- | --- |
| Example 1 | 3.3 (0.2 wt. %) | 9.8 | 1.4 | 13.1 | 1.4 |
| Comparative Example 1 | 1.5 (0.09 wt. %) | 4.4 | 0.6 | 0 | 6.5 |

MeOAc = Methyl acetate

EXAMPLE 2

The procedures of this invention were carried out using the experimental equipment shown in FIG. 1. Titanium pressure-resisting reactor (1) of 10 l capacity equipped with reflux condenser device having a condensate outlet (7), a stirring means, a heating device, a starting material inlet, a solvent inlet, an air inlet, a reaction slurry outlet and an off-gas outlet was charged with a solvent formulation having the following composition:

| Acetic acid | 2,990 g |
| --- | --- |
| Cobalt acetate (tetrahydrate) | 4.44 g (330 ppm as Co) |
| Manganese acetate (tetrahydrate) | 4.68 g (330 ppm as Mn) |
| Hydrobromic acid (aqueous 47% solution) | 6.70 g (1,000 ppm as Br) |
| Water | 154 g (5% water content) |

In the above composition, all parts and percentage are based on the total weight of the formulation.

On the other hand, stainless steel pressure-resisting absorption column (2) of 10 l capacity equipped with an off-gas sparging inlet, an off-gas outlet, an acetic acid inlet and an acetic acid outlet was charged with 5 l of glacial acetic acid.

First reaction

A reaction was carried out in reactor (1) for 2 hours under such conditions that the temperature was 210° C., the pressure, 22 kg/cm² and the stirrer speed, 500 r.p.m., while para-xylene was supplied to reactor (1) at a rate of 500 g/hr. and simultaneously air was passed therethrough at such a rate that the oxygen content of the oxidation off-gas was kept at 4% by volume, thereby a terephthalic acid slurry being prepared. Subsequently the reaction was continued for an additional 24 hours under the same conditions of temperature, pressure and stirring with para-xylene and air being supplied in the same way. During this period, a solvent formulation having the same composition as above and glacial acetic acid were additionally supplied at rates of 1,500 g/hr, and 650 g/hr., respectively, while the condensate was withdrawn at a rate of 650 g/hr. through the condensate outlet (7) for the reflux condensate and the reaction slurry was also withdrawn intermittently from reactor (1) at intervals of 30 minutes to such a level that the volume of the slurry in the reactor was 4.5 l. The reaction slurry removed from the reactor was then filtered to separate terephthalic acid precipitates and the filtrate was stored in a tank together with the condensate removed through the takeout line. During the above-mentioned reaction, the oxidation off-gas evolved from reactor (1) was passed through absorption column (2), which was operated at a temperature of 30° C. and a pressure of 25 kg/cm² under stirring at a speed of 150 r.p.m. From two hours after the reaction had been started, glacial acetic acid was supplied to the column at a rate of 500 g/hr., while the acetic acid in the column was intermittently withdrawn at intervals of 30 minutes to such a level that the volume of the acetic acid therein was 5 l. The thus obtained acetic acid which contained methyl acetate absorbed therein was also stored in another tank.

Second reaction

The combined reaction mother liquor and reflux condensate resulting from the first reaction were passed to evaporator (3), in which the liquid components were completely evaporated at 130° C. The vapor was then passed to distillation column (4) for the separation of acetic acid, and distilled therein at an overhead temperature of 100° C. so as to recover acetic acid from the bottom. The overhead liquid comprising a mixture of water and methyl acetate was then passed to distillation column (5) used for the separation of methyl acetate and distilled therein at an overhead temperature of 57° C. to recover methyl acetate from the overhead. The thus recovered methyl acetate was combined with the acetic acid which was obtained from the absorption column in the first reaction and which contained methyl acetate absorbed therein. In addition, the catalyst components and fresh acetic acid were added so as to prepare a solvent formulation having the same composition as the foregoing except that 23.6 g of methyl acetate was also present for each 1,500 g amount of the formulation. Using the thus prepared solvent formulation, the reaction was carried out for 10 hours under the same conditions as in the first reaction. The amount of methyl acetate formed in this second reaction was determined, thereby the results shown in Table 2 being obtained.

Comparative Example 2

The amount of methyl acetate formed in the first reaction of Example 2 was determined. The results are also given in Table 2.

EXAMPLE 2

|  | MeOAc in reaction mother liquor (g/hr.) | MeOAc absorbed in acetic acid (g/hr.) | MeOAc in reflux condensate (g/hr.) | MeOAc in absorption column off-gas[1] (g/hr.) | MeOAc supplied (g/hr.) | MeOAc formed[2] (g/hr.) |
|---|---|---|---|---|---|---|
| Example 2 | 5.0 (0.3 wt. %) | 14.4 | 4.2 | 2.0 | 23.6 | 2.0 |
| Comparative Example 2 | 2.8 (0.17 wt. %) | 8.1 | 2.1 | 1.2 | 0 | 14.2 |

MeOAc = Methyl acetate (1) Methyl acetate present in the oxidation off-gas after it has been subjected to absorption treatment with acetic acid.

(2) The amount of methyl acetate formed was calculated by subtracting the amount of supplied methyl acetate from the total amount of methyl acetate removed out of the reactor.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for producing terephthalic acid by oxidizing para-xylene with molecular oxygen in acetic acid as a solvent in the presence of a catalyst system containing cobalt, manganese and bromine, the improvement for suppressing the formation of the by-product methyl acetate, which comprises: separating solid terephthalic acid from the terephthalic acid slurry resulting from the reaction to form the mother liquor, subjecting the mother liquor to distillation to separate and recover at least a portion of the methyl acetate present therein and then circulating the thus recovered methyl acetate into the reactor.

2. The process of claim 1, wherein substantially all of the methyl acetate present in the gas evolved from the reactor is recovered and circulated into the reactor.

3. The process of claim 1, wherein substantially all of the methyl acetate contained in the mother liquor is recovered and circulated into the reactor.

4. The process of claim 1, wherein methyl acetate is recovered by (1) evaporating the mother liquor to vaporize liquid materials, (2) distilling the vapors in a distillation column for use in acetic acid separation to recover acetic acid from the bottom and a water-methyl acetate mixture from the overhead, and then distilling the water-methyl acetate mixture in a distillation column for use in methyl acetate separation to recover water from the bottom and methyl acetate from the overhead.

5. The process of claim 1, wherein the reaction temperature is in the range of 150° to 250° C., the reaction pressure is in the range of 10 to 30 kg/cm$^2$ and the residence time is in the range of 30 to 200 minutes.

6. The process of claim 1, wherein the cobalt compound is present at the level of 100 to 500 ppm (as Co metal), the manganese compound at the level of 50 to 1,000 ppm (as Mn metal) and the bromine compound at the level of 500–3,000 ppm (as Br), each component in the catalyst being based on the amount of acetic acid solvent.

7. The process of claim 1, wherein the water content in the reaction system is kept at 5 to 14 percent by weight by taking out of the reaction system a portion of the condensate obtained by condensing the gas evolved from the reactor.

8. The process of claim 7, wherein methyl acetate contained in the condensate which is taken out of the reaction system is recovered.

9. The process of claim 8, wherein methyl acetate is recovered by distilling the mother liquor along with the condensate which is taken out of the reaction system.

* * * * *